United States Patent
Kabir et al.

(10) Patent No.: US 9,700,872 B1
(45) Date of Patent: Jul. 11, 2017

(54) SUPERPOLAR CHROMATOGRAPHIC STATIONARY PHASES AND EXTRACTION SORBENTS AND THEIR METHODS OF SYNTHESIS

(71) Applicants: Abuzar Kabir, Dhaka (BD); Kenneth G. Furton, Homestead, FL (US)

(72) Inventors: Abuzar Kabir, Dhaka (BD); Kenneth G. Furton, Homestead, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 15/200,224

(22) Filed: Jul. 1, 2016

(51) Int. Cl.
 *B01J 20/28* (2006.01)
 *B01J 20/30* (2006.01)
 (Continued)

(52) U.S. Cl.
 CPC ............ *B01J 20/288* (2013.01); *B01D 15/22* (2013.01); *B01D 15/3804* (2013.01);
 (Continued)

(58) Field of Classification Search
 CPC .. B01J 20/288; B01J 20/3085; B01J 20/3242; B01J 2220/86; B01J 20/282; B01J 20/283; B01J 20/284; B01J 20/285; B01J 20/286; B01J 20/291; B01J 2220/48; B01J 2220/4806; B01J 2220/4812; B01J 2220/4825; B01J 2220/4831; B01D 15/22; B01D 15/08; B01D 15/26; B01D 15/36; B01D 15/368; B01D 15/38; B01D 15/3804; B01D 15/3828; B01D 15/3885;
 (Continued)

(56) References Cited

U.S. PATENT DOCUMENTS 5,637,135 A * 6/1997 Ottenstein .............. B01J 20/285
 55/524
6,251,280 B1 * 6/2001 Dai .................... B01J 20/28083
 210/198.2

(Continued)

OTHER PUBLICATIONS

Publication by Guido Kickelbick, "Concepts for the incorporation of inorganicbuilding blocks into organic polymers on a nanoscale", Progress in Polymer Science, vol. 28, 2003, pp. 83-114.*

(Continued)

*Primary Examiner* — Joseph Drodge
(74) *Attorney, Agent, or Firm* — Saliwanchik, Llyod & Eisenschnk (57) ABSTRACT

A superpolar sorbent network is a sol-gel network of at least one metal oxide precursor condensed and at least one polyhydroxy molecule. The metal oxide precursor is a silicate precursor, aluminate precursor, titanate precursor, zirconate precursor, germinate precursor, or any combinations thereof, and the polyhydroxy molecule has a multiplicity of hydroxyl groups. The polyhydroxy molecule can be an organic molecule derived from nature. The superpolar sorbent network can be used as a particulate or bulk sorbent for sampling or removal of analytes or contaminants from an environment or can be coated on a tube or particulate substrate for use as a chromatographic stationary phase.

15 Claims, 5 Drawing Sheets

(51) Int. Cl.
| | |
|---|---|
| B01J 20/32 | (2006.01) |
| B01D 15/38 | (2006.01) |
| B01D 15/36 | (2006.01) |
| B01D 15/22 | (2006.01) |
| B01D 53/04 | (2006.01) |
| B01D 59/26 | (2006.01) |
| B01D 71/02 | (2006.01) |
| B01D 71/08 | (2006.01) |
| B01D 71/70 | (2006.01) |
| B01J 20/288 | (2006.01) |
| B01J 20/281 | (2006.01) |
| G01N 30/02 | (2006.01) |

(52) U.S. Cl.
CPC ......... B01D 15/3885 (2013.01); B01D 53/04 (2013.01); B01D 59/26 (2013.01); B01D 71/027 (2013.01); B01D 71/08 (2013.01); B01D 71/70 (2013.01); B01J 20/3085 (2013.01); B01J 20/3242 (2013.01); G01N 30/48 (2013.01); *B01J 2220/86* (2013.01); *G01N 2030/025* (2013.01)

(58) Field of Classification Search
CPC ............ B01D 2015/3838; B01D 53/02; B01D 53/025; B01D 53/04; B01D 59/26; B01D 63/01; B01D 63/021; G01N 30/48; G01N 2030/025; G01N 2030/486
USPC ... 210/198.2, 500.21, 500.25, 500.27, 502.1, 210/511, 656; 502/401, 405, 407, 411, 502/414; 96/4, 14, 101, 108
See application file for complete search history.

(56) References Cited

U.S. PATENT DOCUMENTS

| | | | |
|---|---|---|---|
| 8,685,240 B2* | 4/2014 | Malik | B01D 15/206 210/198.2 |
| 9,283,544 B2* | 3/2016 | Kabir | G01N 1/405 |
| 2004/0211730 A1* | 10/2004 | Zhang | B01J 20/103 210/656 |
| 2005/0242038 A1* | 11/2005 | Chen | B01J 20/103 210/656 |
| 2006/0131238 A1* | 6/2006 | Xu | B01J 20/28042 210/656 |
| 2007/0062874 A1* | 3/2007 | Malik | B01D 15/206 210/656 |
| 2007/0207484 A1* | 9/2007 | Brook | A61K 47/48961 435/6.12 |
| 2011/0189071 A1* | 8/2011 | Ying | C01B 37/02 423/335 |
| 2014/0338429 A1* | 11/2014 | Isaac | B01D 15/327 73/61.52 |

OTHER PUBLICATIONS

Kabir, A. et al., Capillary microextraction on sol-gel dendrimer coatings, *Journal of Chromatography A*, 2004, pp. 1-11, vol. 1034, No. 1-2.

Ali, I. et al., "Monolithic Silica Stationary Phases in Liquid Chromatography," *Journal of Chromatographic Science*, Jul. 2009, pp. 432-442, vol. 47.

* cited by examiner

SUPERPOLAR CHROMATOGRAPHIC STATIONARY PHASES AND EXTRACTION SORBENTS AND THEIR METHODS OF SYNTHESIS

BACKGROUND OF INVENTION

Poly(ethylene glycol) is commonly used as a polar polymer for immobilization on a substrate's surface. These substrates are used as stationary phases for chromatographic separations and as extraction sorbents. However, poly(ethylene glycol) has insufficient polarity for absorption and analysis of many highly polar analytes. Immobilization of polar polymers, including poly(ethylene glycol), on a substrate's surface is considered a challenge to surface chemists. In a conventional coating process, a thin coating of the polymer is deposited on the substrate's surface, followed by free-radical cross-linking reaction that forms a mesh-like network to anchor the coating to the surface. Bound poly (ethylene glycol) behaves like a pseudo-liquid that retains target analytes via dissolution. The dissolution of analytes in a highly viscous solid can be a slow process that requires long extraction time to reach equilibrium. Absent chemical linkage between the polymer film and the substrate surface, the sorbent coating is vulnerable to being washed out by organic solvents nor can the coated substrate be exposed to high temperature; as when heated for thermal desorption after an analyte extraction or when employed as a chromatographic stationary phase. Incorporation of poly(ethylene glycol) polymer in the sol-gel matrix (sol-gel coating technology) improves solvent resistance and thermal stability of the composite material.

Nevertheless, the limited polarity of poly(ethylene glycol) remains a problem when employed to target very highly polar analytes. To the end a simple and environmental friendly approach of immobilization of highly polar molecules to a metal oxide network for use as superpolar stationary phase and/or extraction sorbent is desirable. Such a composition can have properties derived from being a sol-gel inorganic/hybrid organic-inorganic polymeric network that can be formulated to display adjustable porosity, tunable selectivity, high thermal stability, solvent stability, and wide pH stability.

BRIEF SUMMARY

An embodiment of the invention is directed to a superpolar sorbent network, comprising a sol-gel network of at least one metal oxide precursor condensed with at least one polyhydroxy molecule. The metal oxide precursor can be a silicate precursor, aluminate precursor, titanate precursor, zirconate precursor, germinate precursor, or any combinations thereof. The silicate precursor can be a tetraalkoxysilane, trialkoxysilane, or a combination of at least one of the tetraalkoxysilane and trialkoxysilane with a dialkoxysilane. The polyhydroxy molecule comprises an organic molecule comprising a multiplicity of hydroxyl groups. The polyhydroxy molecule is sucrose, sucrose-6-phosphate, sucrose 6F-phosphate, 2-cyanoethyl sucrose, sucralose, 1-ketose, UDP-alpha-D-glucose, uridine diphosphate glucose, sorbitol, or any mixture thereof. The silicate precursors can include an unsubstituted or substituted aryltrialkoxysilane or an unsubstituted or substituted alkyltrialkoxysilane.

In an embodiment of the invention, the superpolar sorbent network is a component of a sampling device or an analytical device. The sampling device can be an extraction device, and the analytical device can be a chromatography stationary phase. The extraction device can be a fiber superpolar microextraction fiber, superpolar microextraction tube, superpolar microextraction membrane, superpolar microextraction stir bar, superpolar microextraction fabric, superpolar microextraction capsule, or superpolar microextraction vial. The extraction device can be a solid phase extractor selected from a matrix solid phase dispersant, a magnetic solid phase extractor, or a dynamic fabric phase sorptive extractor. The analytical device is a gas chromatograph or a liquid chromatograph stationary phase.

An embodiment of the invention is directed to a method of preparing the superpolar sorbent network where at least one metal oxide precursor, at least one polyhydroxy molecule, water, a catalyst, and, optionally, a solvent are combined for the hydrolysis of the precursors to a sol that upon condensing the hydrolyzed metal oxide precursors and the polyhydroxy molecules, the superpolar sorbent network forms. The sol can be heated to facilitate condensation to the network. The sol can be coated on a substrate prior to network formation or complete condensation can occur in bulk. Substrates that can be used are metal oxide particles, metal tubes, silica fibers, fabrics, glass tubes, glass sheets, or vials.

DETAILED DISCLOSURE

Embodiments of the invention are directed to superpolar sorbent networks that can be employed as coatings or bulk resins for use as highly polar chromatographic stationary phases and adsorption sorbents. These superpolar sorbent networks are metal oxide-organic hybrids including sol-gel networks that comprise sucrose, ketose, uridine diphosphate glucose, or other highly polar polyhydroxy molecules. The polyhydroxy molecule can be derived from natural materials or can be synthetic molecules, such as oligomers of vinyl alcohol. These highly polar polyhydroxy molecules are immobilized via sol-gel process on the substrate. This sol-gel coating can be on the inside a fused silica capillary for use as a gas chromatographic stationary phase or as an in-tube solid phase microextractor. This sol-gel coating can be on the outside of a fused silica fiber or a metal rod for use as a solid phase microextraction sorbent. This sol-gel coating can be on the surface of silica, alumina, titania, zirconia, germania, or other metal oxide particles for use as liquid chromatographic stationary phase. This sol-gel resin can be prepared in-situ as a monolithic bed inside a wide bore tube for use as a liquid chromatographic stationary phase. Different shapes, sizes and geometries can be fabricated that are well suited to function as solid phase extraction sorbent particles as required of the final application and delivery mechanism. A sol solution can be a homogenous mixture or a dispersion that additionally can include at least one sol-gel precursor that is capable of providing London dispersion type forces and/or at least one sol-gel precursor capable of exerting pi-pi interaction with target analytes. The new sorbents and chromatographic stationary phases formed from the coatings, according to embodiments of the invention, interact with various target analytes via one or more dipole-dipole interactions, hydrogen bonding, London dispersion forces, and pi-pi interactions.

In an embodiment of the invention, the high polarity of sucrose and/or other polar polyhydroxy molecules with various molecular interaction mechanisms can be incorporated into a polymeric network via sol-gel processing in a simple, highly reproducible, and environmentally benign manner. The highly polar chromatographic stationary phases and adsorption sorbents, for solid phase extraction (exhaustive extraction) or solid phase microextraction (equilibrium driven extraction), can be effectively employed to absorb or analyze polar, medium polar, nonpolar, and polarizable analytes. Examples of the highly polar polyhydroxy molecules that can be incorporated into the sol-gel coating are given in Table 1, below. These molecules can be combined with metal oxide precursors into a sol or partially hydrolyzed and condensed sol to form a composite sol that can be applied to a substrate surface. The use of the small molecules and oligomers have advantages over typical organic polymers that are large and have varying degrees of polydispersity resulting in relatively poor batch-to-batch reproducibly. This reproducibility issue can be largely addressed by using relatively monodispersed polymers and dendrimers, as taught in Kabir, A., et al. "Capillary Microextraction on Sol-Gel Dendrimer Coatings." *Journal of Chromatography A* 2004, 1034(1-2), 1-11, yet such monodispersed polymers are often expensive to employ. The use of monomeric, dimeric, or small oligomeric organic molecules, having relatively fixed molecular weights, optimizes batch-to-batch reproducibility. These organic molecules can also be converted into organically modified inorganic precursors to enhance reaction selectivity for formation of composite material.

TABLE 1

Exemplary polyhydroxy molecules for formation of sols that are converted into metal oxide-organic hybrid sorbents

| Monomer | MW | Empirical Formula | Log $K_{ow}$ |
|---|---|---|---|
| Ethylene glycol | 62.06 | $C_4H_{10}O_4$ | −1.4 |
| Sucrose | 342.30 | $C_{12}H_{22}O_{11}$ | −3.7 |
| Sucrose-6-phosphate | 422.28 | $C_{12}H_{23}O_{14}P$ | −5.3 |
| Sucrose-6F-phosphate | 420.26 | $C_{12}H_{21}O_{14}P^{-2}$ | −5.5 |

TABLE 1-continued

Exemplary polyhydroxy molecules for formation of sols that are converted into metal oxide-organic hybrid sorbents

| Monomer | MW | Empirical Formula | Log $K_{ow}$ |
|---|---|---|---|
| 2-Cyanoethyl sucrose | 395.36 | $C_{15}H_{25}NO_{11}$ | −4.0 |
| Sucralose | 397.63 | $C_{12}H_{19}C_{13}O_8$ | −1.5 |
| 1-Ketose | 504.44 | $C_{18}H_{32}O_{16}$ | −5.5 |
| UDP-alpha-D-glucose | 564.29 | $C_{15}H_{22}N_2O_{17}P_2^{-2}$ | −6.5 |
| Uridine Diphosphate Glucose | 566.30 | $C_{15}H_{24}N_2O_{17}P_2$ | −6.3 |
| Sorbitol | 182.17 | $C_6H_{14}O_6$ | −3.1 |

The metal oxide precursors for inclusion in the sol can be selected from precursors for silicates, aluminates, titanates, zirconates, germinates, other metal oxide precursors, or any mixture thereof. The nature of the metal oxide precursors is herein exemplified by silanes, but the equivalent with other metals and number of substituents can be readily appreciated by practitioners of the art. For silicate based superpolar sorbents, the precursors can be a combination of tetraalkoxysilanes, trialkoxysilanes, and dialkoxysilanes. The proportion of tetraalkoxysilanes can be 0-100 weight percent. The proportion of triakoxysilanes can be 0 to 100 weight percent. The proportion of dialkoxysilanes can be 0 to 99 weight percent.

Tetraalkoxysilanes, can be, but are not limited to, tetramethoxysilane and tetraethoxysilane. Tetraalkoxysilanes can be used exclusively with the polar organic molecules or with mixtures of trialkoxysilanes or dialkoxysilanes. The trialkoxysilanes can be, but are not limited to, alkyltrialkoxysilanes, such as methyltrimethoxysilanes, ethyltrimethoxysilanes, methyltriethoxysilanes, ethyltrialkoxysilanes, or any $C_xH_{2x+1}Si(OC_yH_{2y+1})_3$ silane, where x is 1 to 20 and y is 1 to 3. The alkyltrialkoxy silane can have a substituted alkyl group, for example, but not limited to, 3-aminoporpyltrimethoxysilane, 2-aminopropyltrimethoxysilane, 3-hydroxytrimethoxysilane, or any alkyl group containing one or more ether, hydroxyl, carboxylic acid, carboxylic amide, amino, alkylamino, dialkylamino, cyano group, or any other polar or non-polar groups. The trialkoxysilanes can be aryltrialkoxysilanes, such as, but not limited to, phenyltrimethoxysilane, phenyltriethoxysilane, naphtyltrimethoxysilane, naphtyltriethoxysilane, or any other substituted or unsubstituted aryl trialkoxysilane.

The dialkoxysilanes can be dialkyldialkoxysilanes, diaryldialkoxysilane, or alkylarydialkoxysilanes. Dialkyldialkoxysilanes can be, for example, but not limited to, dimethyldimethoxiysilanes, diethyldimethoxysiloxanes, methylethyldimethoxysilanes, dimethyldiethoxiysilanes, diethyldiethoxysiloxanes, methylethyldiethoxysilanes, or any $(C_xH_{2x+1})_2Si(OC_yH_{2y+1})_2$ silane, where x is independently 1 to 20 and y is 1 to 3. The dialkyldialkoxyslanes can have one or two substituted alkyl groups, where the alkyl group contains one or more ether, hydroxyl, carboxylic acid, carboxylic amide, amino, alkylamino, dialkylamino, cyano group, or any other polar or non-polar group.

The superpolar sorbent is prepared by the condensation of the silanes with a molecule that has multiple hydroxyl groups attached to a hydrocarbon framework, a polyhydroxy molecule. The condensation is carried out in the presences of water, where the proportion of water to alkoxy groups of the tetraalkoxysilanes, trialkoxysilanes, and dialkoxysilanes is less than one to two, such as those shown in Table 1. The molecules with multiple hydroxyl groups have a log $K_{ow}$, the partitioning coefficient between octanol and water, as indicated in Table 1, having a log $K_{ow}$, for example, less than −2 is useful for superpolar sorbent preparation.

Figure 1A:
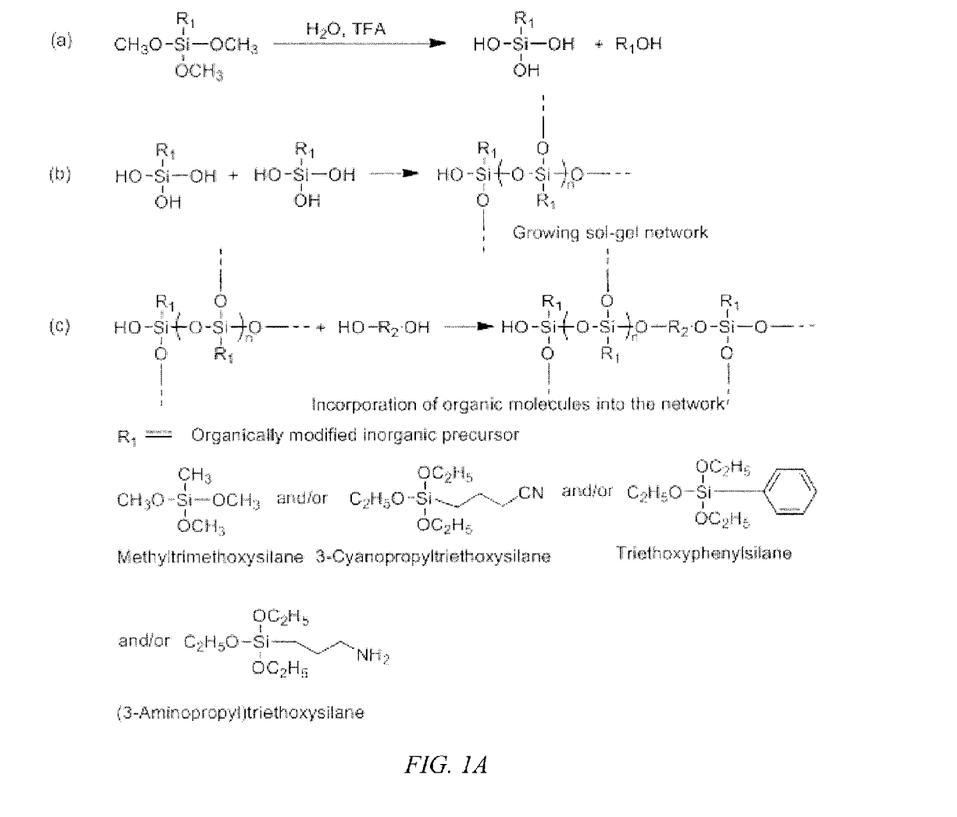
FIG. 1A is a reaction scheme for the formation of a superpolar sorbent network, according to an embodiment of the invention.
Figure 1B:
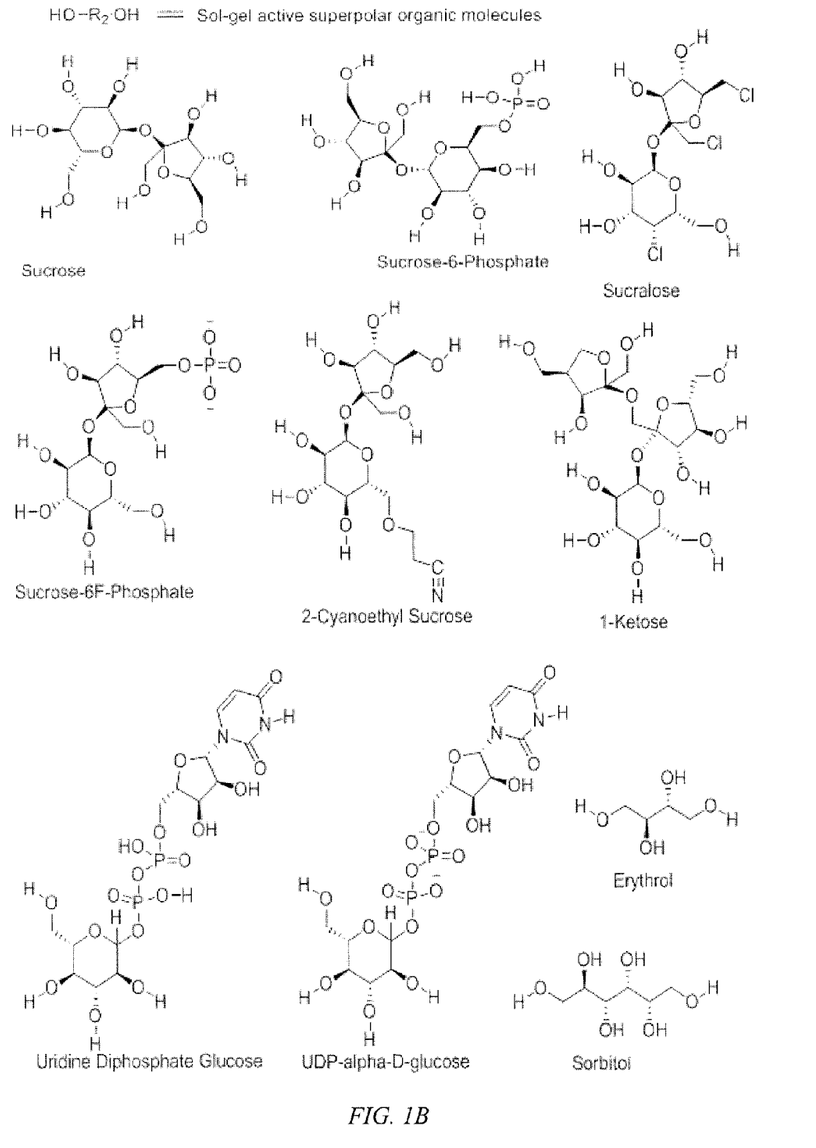
FIG. 1B are chemical structures of polyhydroxy molecules that can be used for the formation of the superpolar sorbent network, according to an embodiment of the invention, where HO—$R_2$—OH is the polyhydroxy molecule used for formation of the superpolar sorbent network.

In an embodiment of the invention, the superpolar sorbent is prepared by an acid catalyzed hydrolysis and condensation of the silanes in the presence of water and the polyhydroxy molecules, as illustrated in FIG. 1A with exemplary polyhydroxy molecules of Table 1, illustrated in FIG. 1B. The acid can be a Bronsted acid such as trifluoroacetic acid (TFA), as shown in FIG. 1A, or any strong acid, such as hydrochloric acid, sulfuric acid, or hydrofluoric acid. A solvent, for example ethanol, or any polar organic solvent, for example, but not limited to dimethylsulfoxide (DMSO), methylene chloride, chloroform, or methanol, can be included in the sol. The sol is prepared and either further condensed into a particle form or a substrate, which can be particulate, fabric or of any structure, can be contacted with the sol solution. Contact can be by suspension of the substrate in the sol, painting the substrate with the sol, or spraying the substrate with the sol. The sol is finally condensed into a network. In another embodiment of the invention, the catalysis can be by base rather than acid. Base catalysts can be sodium hydroxide, potassium hydroxide, or amine, such as pyridine, trimethylamine, or ammonia.

Figure 2:
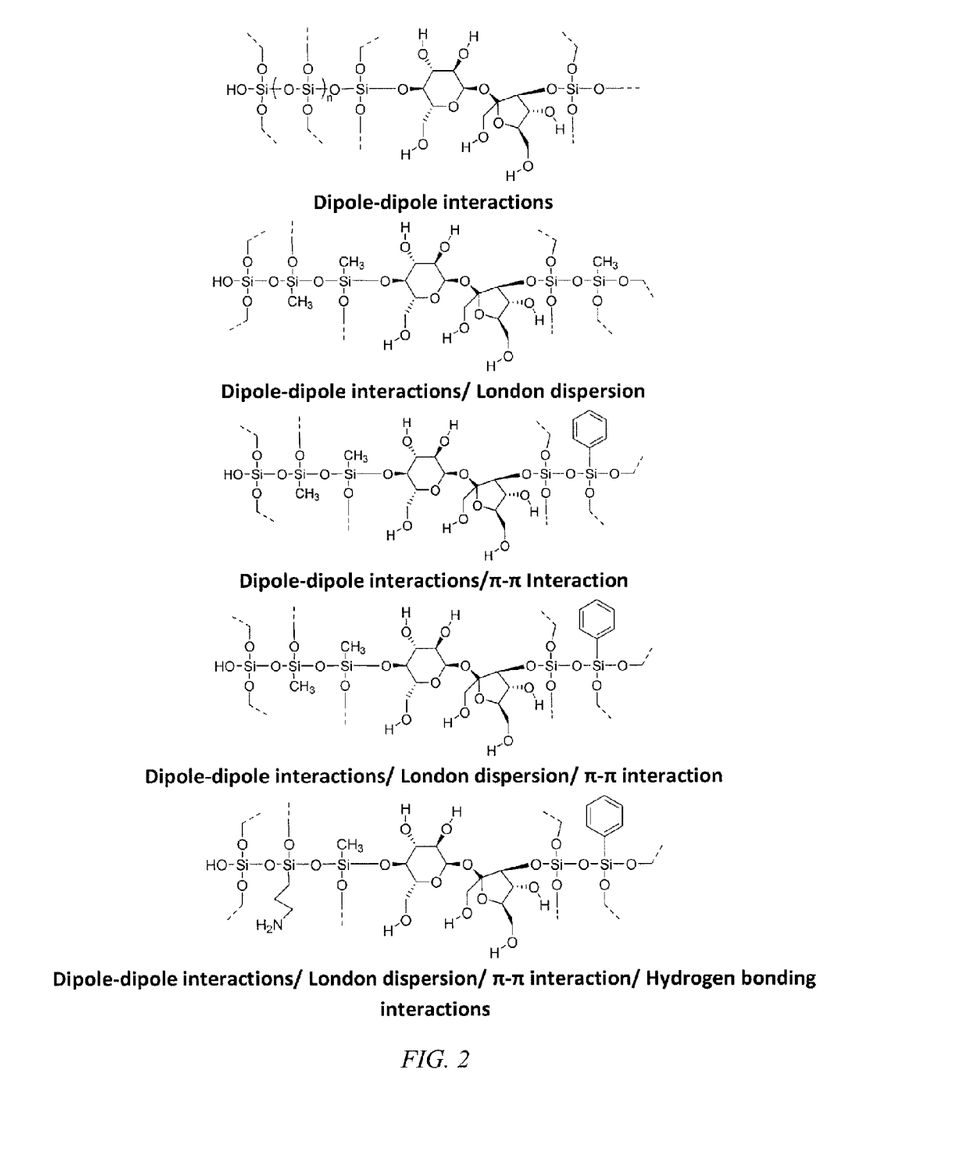
FIG. 2 shows some exemplary structures of superpolar sorbent networks that are formed from sucrose and various tetraalkoxysilanes and trialkoxysilanes to permit various interactions for the absorption of analytes, according to embodiments of the invention.

The superpolar sorbent network can have various structures that form interactions with the substrate molecules, in addition to the dipole-dipole interactions, which include hydrogen bonding interactions, ion-dipole interactions, or ion-pairing interactions, for purposes of the invention, that are provided by the incorporation of the polyhydroxy molecules with a tetralkoxysilane derived network, by choice of the trialkoxysilanes and dialkoxysilanes employed, groups that can also interact by London dispersion forces, π-π interactions, and additional dipole-dipole, ion-dipole, or ion pairing interactions can be included. Various combinations are illustrated by structures employing sucrose in FIG. 2. These idealized structures of FIG. 2 do not show the random placement of units within the network, uncondensed silanols that form upon hydrolysis but are not condensed, unhydrolyzed alkoxysilane bonds, nor are the various possibilities of differing patterns and degrees of condensation of the sucrose illustrated in FIG. 2. It is to be understood that these structures only illustrate the types of units within exemplary networks.

Fields of study such as: metabolomics; environmental chemistry; analytical and forensic toxicology; clinical chemistry; drug discovery; and food quality and safety monitoring must deal with highly polar analytes present in a variety of sample matrices with high volume of matrix interferents. Due to the strong interactions between water molecules and polar analytes, it is extremely difficult to break these water-polar analyte interactions in order to isolate and concentrate them into a solid sorbent for subsequent instrumental analysis. The lack of highly polar sorbents has seriously impaired the advancement of these fields. Highly sensitive analytical instruments complemented with powerful operating software have not resolved problems originating from sample preparation difficulties. The superpolar sorbents could overcome inabilities due to limitations of sample preparation techniques, and replace a large number of ineffective materials currently being used as polar sorbents. For example, the United States Environmental Protection Agency (EPA) has a priority list of compounds where monitoring and detection are important. As can be seen in Table 2, below, one third of the top 100 chemicals on this list have a $K_{ow}$ of about 2 or less, which suggests the use of the superpolar sorbents.

TABLE 2

Top 100 EPA Priority Pollutants

| Compound | Molecular Weight | Formula | Log $K_{ow}$ | H Bond Donor | H Bond Acceptor |
|---|---|---|---|---|---|
| Acenaphthene | 154.207 | $C_{12}H_{10}$ | 3.9 | 0 | 0 |
| Acrolein | 56.063 | $C_3H_4O$ | −0.01 | 0 | 1 |
| Acrylonitrile | 53.062 | $C_3H_3N$ | 0.25 | 0 | 1 |
| Benzene | 78.111 | $C_6H_6$ | 2.1 | 0 | 0 |
| Benzidine | 184.237 | $C_{12}H_{12}N_2$ | 1.34 | 2 | 2 |
| Carbon tetrachloride | 153.823 | $CCl_4$ | 2.83 | 0 | 0 |
| Chlorobenzene | 112.557 | $C_6H_5Cl$ | 2.84 | 0 | 0 |
| 1,2,4-Trichlorobenzene | 181.4470 | $C_6H_3Cl_3$ | 4.02 | 0 | 0 |
| Hexachlorobenzene | 284.7822 | $C_6Cl_6$ | 5.7 | 0 | 0 |
| 1,2-Dichloroethane | 98.9592 | $C_2H_4Cl_2$ | 1.5 | 0 | 0 |
| 1,1,1-Trichloroethane | 133.4042 | $C_2H_3Cl_3$ | 2.4 | 0 | 0 |
| Hexachloroethane | 236.7394 | $C_2Cl_6$ | 4.1 | 0 | 0 |
| 1,1-Dichloroethane | 98.9592 | $C_2H_4Cl_2$ | 1.5 | 0 | 0 |
| 1,1,2-Trichloroethane | 133.4042 | $C_2H_3Cl_3$ | 2.4 | 0 | 0 |
| 1,1,2,2-Tetrachloroethane | 167.8493 | $C_2H_2Cl_4$ | 2.4 | 0 | 0 |
| Chloroethane | 64.5141 | $C_2H_5Cl$ | 1.2 | 0 | 0 |
| Bis(2-Chloroethyl)ether | 143.0117 | $C_4H_8Cl_2O$ | 1.3 | 0 | 1 |
| 2-Chroethyl vinyl ether | 106.5508 | $C_4H_7ClO$ | 1.4 | 0 | 1 |
| 2-Chloronaphthalene | 162.6156 | $C_{10}H_7Cl$ | 4.1 | 0 | 0 |
| 2,4,6-Trichlorophenol | 197.4464 | $C_6H_3Cl_3O$ | 3.7 | 1 | 1 |
| Parachlorometacresol | 142.5829 | $C_7H_7ClO$ | 3.1 | 1 | 1 |
| Chloroform | 119.3776 | $CHCl_3$ | 2.3 | 0 | 0 |
| 2-Chlorophenol | 128.5563 | $C_6H_5ClO$ | 2.1 | 1 | 1 |
| 1,2-Dichlorobenzene | 147.0020 | $C_6H_4Cl_2$ | 3.4 | 0 | 0 |
| 1,3-Dichlorobenzene | 147.0020 | $C_6H_4Cl_2$ | 3.5 | 0 | 0 |
| 1,4-Dichlorobenzene | 147.0020 | $C6H_4Cl_2$ | 3.4 | 0 | 0 |
| 3,3-Dichlorobenzidine | 253.1272 | $C_{12}H_{10}Cl_2N_2$ | 3.5 | 2 | 2 |
| 1,1-Dichloroethylene | 96.9434 | $C_2H_2Cl_2$ | 2.3 | 0 | 0 |
| 1,2-Transdichloroethylene | 96.9434 | $C_2H_2Cl_2$ | 1.9 | 0 | 0 |
| 2,4-Dichlorophenol | 163.0014 | $C_6H_4Cl_2O$ | 3.1 | 1 | 1 |
| 1,2-Dichloropropane | 112.9857 | $C_3H_6Cl_2$ | 1.8 | 0 | 0 |
| 1,3-Dichloropropylene | 110.9699 | $C_3H_4Cl_2$ | 1.7 | 0 | 0 |
| 2,4-Dimethylphenol | 122.1644 | $C_8H_{10}O$ | 2.3 | 1 | 1 |

TABLE 2-continued

Top 100 EPA Priority Pollutants

| Compound | Molecular Weight | Formula | Log $K_{ow}$ | H Bond Donor | H Bond Acceptor |
|---|---|---|---|---|---|
| 2,4-Dinitrotoluene | 182.1335 | $C_7H_6N_2O_4$ | 2 | 0 | 4 |
| 2,6-Dinitrotoluene | 182.1335 | $C_7H_6N_2O_4$ | 2.1 | 0 | 4 |
| 1,2-Diphenylhydrazine | 184.1335 | $C_{12}H_{12}N_2$ | 2.9 | 2 | 2 |
| Ethylbenzene | 202.2506 | $C_8H_{10}$ | 3.1 | 0 | 0 |
| Fluoranthene | 202.2506 | $C_{16}H_{10}$ | 5.2 | 0 | 0 |
| 4-Chlorophenyl phenyl ether | 204.6523 | $C_{12}H_9ClO$ | 4.3 | 0 | 1 |
| 4-Bromophenyl phenyl ether | 249.1033 | $C_{12}H_9BrO$ | 4.4 | 0 | 1 |
| Bis(2-Chloroisopropyl)ether | 171.0649 | $C_6H_{12}Cl_2O$ | 2.7 | 0 | 1 |
| Bis(2-Chloroethoxy)methane | 173.0377 | $C_5H_{10}Cl_2O_2$ | 1.2 | 0 | 2 |
| Methylene Chloride | 84.9426 | $CH_2Cl_2$ | 1.5 | 0 | 0 |
| Methyl chloride | 50.4875 | $CH_3Cl$ | 0.8 | 0 | 0 |
| Methyl bromide | 94.9385 | $CH_3Br$ | 1 | 0 | 0 |
| Bromoform | 252.7306 | $CHBr_3$ | 2.8 | 0 | 0 |
| Dichlorobromomethane | 163.8286 | $CHBrCl_2$ | 2.4 | 0 | 0 |
| Chlorodibromomethane | 208.2796 | $CHBr_2Cl$ | 2.6 | 0 | 0 |
| Hexachlorobutadiene | 260.7608 | $C_4Cl_6$ | 4.8 | 0 | 0 |
| Hexachlorocyclopentadiene | 272.7715 | $C_5Cl_6$ | 5 | 0 | 0 |
| Isophorone | 138.2069 | $C_9H_{14}O$ | 1.6 | 0 | 1 |
| Naphthalene | 128.1705 | $C_{10}H_8$ | 3.3 | 0 | 0 |
| Nitrobenzene | 123.1094 | $C_6H_5NO_2$ | 1.9 | 0 | 2 |
| 2-Nitrophenol | 139.1088 | $C_6H_5NO_3$ | 1.8 | 1 | 3 |
| 4-Nitrophenol | 139.1088 | $C_6H_5NO_3$ | 1.9 | 1 | 3 |
| 2,4-Dinitrophenol | 184.1064 | $C_6H_4N_2O_5$ | 1.7 | 1 | 5 |
| 4,6-Dinitro-o-cresol | 198.1329 | $C_7H_6N_2O_5$ | 2.1 | 1 | 5 |
| N-Nitrosodimethylamine | 74.0818 | $C_2H_6N_2O$ | −0.6 | 0 | 3 |
| N-Nitrosodiphenylamine | 198.2206 | $C_{12}H_{10}N_2O$ | 3.1 | 0 | 3 |
| N-Nitrosodi-n-propylamine | 130.1881 | $C_6N_{14}N_2O$ | 1.4 | 0 | 3 |
| Pentachlorophenol | 266.3365 | $C_6HCl_5O$ | 5.1 | 1 | 1 |
| Phenol | 94.1112 | $C_6H_6O$ | 1.5 | 1 | 1 |
| Bis(2-Ethylhexyl)phthalate | 390.5561 | $C_{24}H_{38}O_4$ | 7.4 | 0 | 4 |
| Butyl benzyl phthalate | 312.3597 | $C_{19}H_{20}O_4$ | 4.9 | 0 | 4 |
| Di-N-butyl phthalate | 278.3435 | $C_{16}H_{22}O_4$ | 4.7 | 0 | 4 |
| Di-n-octyl phthalate | 390.5561 | $C_{24}H_{38}O_4$ | 9.1 | 0 | 4 |
| Diethyl phthalate | 222.2372 | $C_{12}H_{14}O_4$ | 2.5 | 0 | 4 |
| Dimethyl phthalate | 194.1841 | $C_{10}H_{10}O_4$ | 1.6 | 0 | 4 |
| Benzo(a)anthracene | 228.2879 | $C_{18}H_{12}$ | 5.8 | 0 | 0 |
| Benzo(a)pyrene | 252.3093 | $C_{20}H_{12}$ | 6 | 0 | 0 |
| Benzo(b)fluoranthene | 252.3093 | $C_{20}H_{12}$ | 6.4 | 0 | 0 |
| Benzo(k)fluoranthene | 252.3093 | $C_{20}H_{12}$ | 6.4 | 0 | 0 |
| Chrysene | 228.2879 | $C_{18}H_{12}$ | 5.7 | 0 | 0 |
| Acenaphthylene | 152.1919 | $C_{12}H_8$ | 3.7 | 0 | 0 |
| Anthracene | 178.2292 | $C_{14}H_{10}$ | 4.4 | 0 | 0 |
| Benzo(ghi)perylene | 276.33 | $C_{22}H_{12}$ | 6.6 | 0 | 0 |
| Fluorene | 166.2185 | $C_{13}H_{10}$ | 4.2 | 0 | 0 |
| Phenanthrene | 178.2292 | $C_{14}H_{10}$ | 4.5 | 0 | 0 |
| Dibenzo(h)anthracene | 278.3466 | $C_{22}H_{14}$ | 6.5 | 0 | 0 |
| Indeno (1,2,3-cd) pyrene | 276.3307 | $C_{22}H_{12}$ | 7 | 0 | 0 |
| Pyrene | 202.2506 | $C_{16}H_{10}$ | 4.9 | 0 | 0 |
| Tetrachloroethylene | 165.8334 | $C_2C_{14}$ | 3.4 | 0 | 0 |
| Toluene | 92.1384 | $C_7H_8$ | 2.7 | 0 | 0 |
| Trichloroethylene | 131.3883 | $C_2HCl_3$ | 2.6 | 0 | 0 |
| Vinyl chloride | 62.4982 | $C_2H_3Cl$ | 1.5 | 0 | 0 |
| Aldrine | 364.9099 | $C_{12}H_8Cl_6$ | 4.5 | 0 | 0 |
| Dieldrin | 380.9093 | $C_{12}H_8C_{16}O$ | 3.7 | 0 | 1 |
| Chlordane | 409.7786 | $C_{10}H_6Cl_8$ | 4.9 | 0 | 0 |
| 4,4-DDT | 354.4863 | $C_{14}H_9Cl_5$ | 6.9 | 0 | 0 |
| 4,4-DDE | 318.0253 | $C_{14}H_8Cl_4$ | 7 | 0 | 0 |
| 4,4-DDD | 320.0412 | $C_{14}H_{10}Cl_4$ | 6.2 | 0 | 0 |
| Alpha-endosulfan | 406.9251 | $C_9H_6Cl_6O_3S$ | 3.8 | 0 | 4 |
| Beta-endosulfan | 406.9251 | $C_9H_6Cl_6O_3S$ | 3.8 | 0 | 4 |
| Endosulfan sulfate | 422.9245 | $C_9H_6Cl_6O_4S$ | 3.7 | 0 | 4 |
| Endrin | 380.9093 | $C_{12}H_8Cl_6O$ | 3.7 | 0 | 1 |
| Endrin aldehyde | 380.9093 | $C_{12}H_8Cl_6O_2$ | 3 | 0 | 1 |
| Heptachlor | 373.3177 | $C_{10}H_5Cl_7$ | 4.3 | 0 | 0 |
| Heptachlor epoxide | 389.3171 | $C_{10}H_5Cl_7O$ | 3.7 | 0 | 1 |
| Alpha-BHC | 290.8298 | $C_6H_6Cl_6$ | 3.8 | 0 | 0 |

Figure 3:
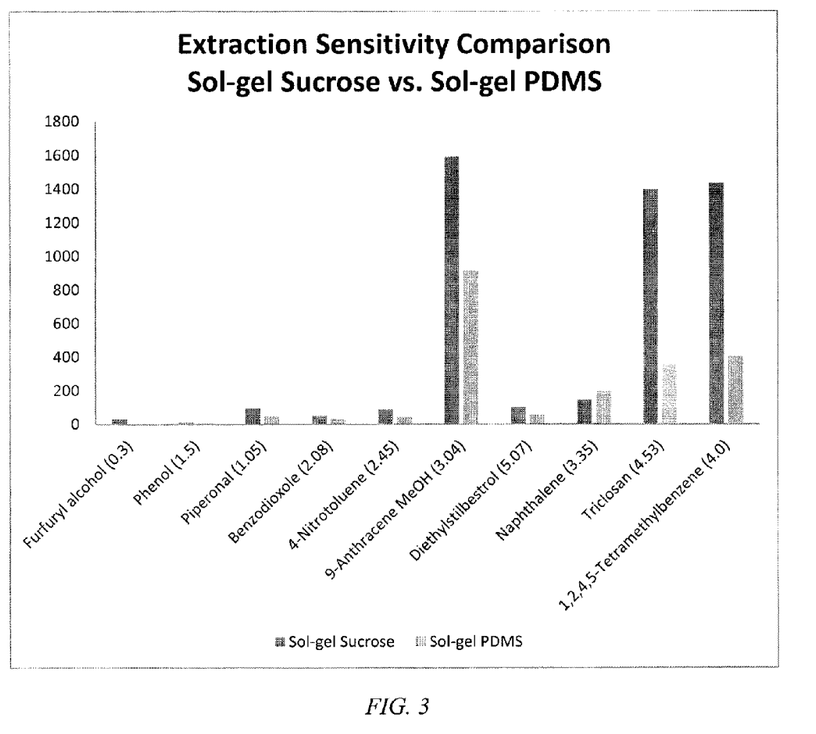
FIG. 3 is a bar chart of the extraction of various analytes using a sol-gel tetramethoxysilane and sucrose superpolar sorbent, according to an embodiment of the invention, and a sol-gel polydimethylsiloxane sorbent, where the difference in heights of the bars reflects the selectivity for the analyte.

The superpolar sorbents, according to embodiments of the invention, are effective at the absorption of polar compounds. For example, the exemplary superpolar sorbent prepared from sucrose and poly(dimethylsiloxane) are compared in FIG. 3, with a variety of analytes that have log $K_{ow}$ having superior absorption in the superpolar sorbent than in the non-polar solvent. The superiority of the sol-gel sucrose derived superpolar sorbent was observed for every analyte with the exception of the analyte naphthalene.

Figure 4A:
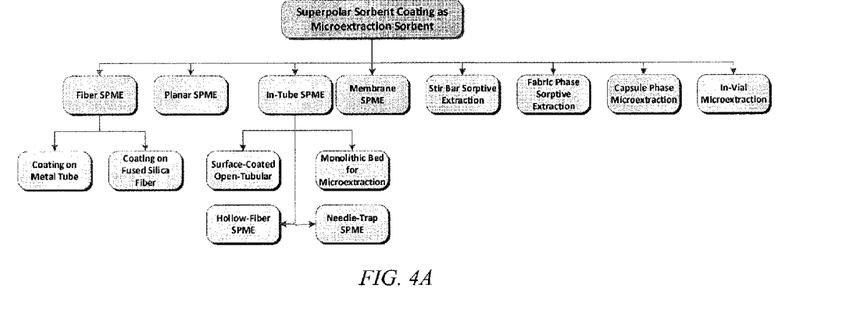
FIG. 4A displays a chart of microextraction sorbent devices, according to an embodiment of the invention, which can be fabricated using the superpolar sorbent networks.
Figure 4B:
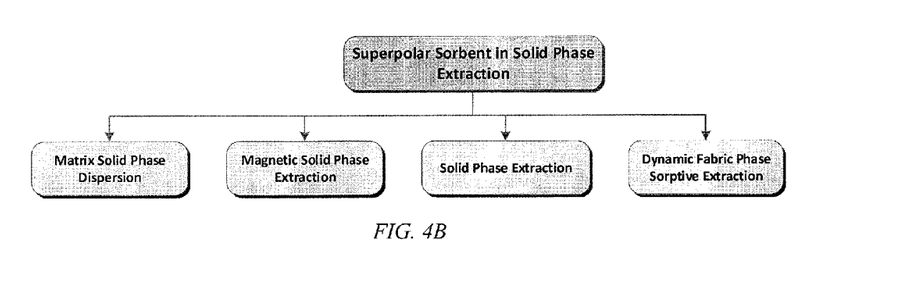
FIG. 4B displays a chart of solid phase extraction devices, according to an embodiment of the invention, which can be fabricated using the superpolar sorbent networks.
Figure 4C:
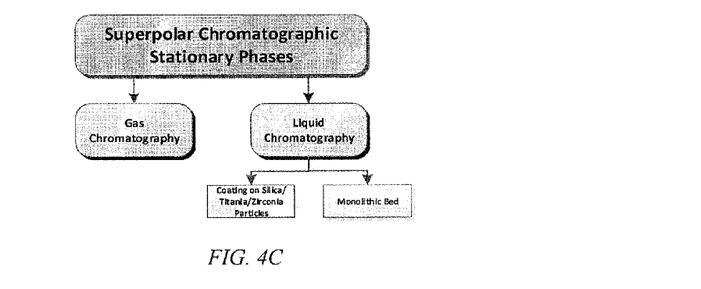
FIG. 4C displays a chart of chromatographic stationary phases for analytical devices, according to an embodiment of the invention, which can be fabricated using the superpolar sorbent networks

The superpolar sorbents can be used in a wide variety of applications. The superpolar absorbents can be coated onto microextraction devices, as indicated in FIG. 4A. The superpolar sorbents can be used for exhaustive extraction, as indicated in FIG. 4B. The superpolar sorbents can be used for stationary phases for chromatographic separation of analytes in a mixture, as indicated in FIG. 4C.

METHODS AND MATERIALS

Superpolar Sol-Gel Sucrose Sorbent Composition Preparation

Sol-Gel Sucrose for a Monolithic Bed or SPE Particles:

A sol was prepared from sucrose (1.00 g), tetramethoxysilane (TMOS) (1000 µL), and 0.1M HF solution (2000 µL) in ethanol (5000 µL). The sol solution ingredients were mixed using a vortex stirrer, and subsequently held still at 50° C., whereupon gelation occurred.

Sol-Gel Sucrose for Thin Film Generation on a Substrate Surface:

A sol was prepared from sucrose (1.00 g), methyltrimethoxysilane (MTMOS) (2.5 mL), and 0.1M 5% aqueous TFA solution (1 mL) in DMSO (5 mL). After thoroughly mixing the sol solution ingredients using a vortex mixer a substrate for sol-gel coating was submerged into the sol solution and the coating unit was kept at 50° C.

All publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A superpolar sorbent network, comprising a sol-gel network of at least one metal oxide precursor condensed with at least one polyhydroxy molecule where the network comprises units with metal-oxygen-metal groups and units with metal-oxygen-carbon groups respectively bonded to the at least one polyhydroxy molecule of one or more of the structures:

and/or where there is a random placement of units within the network, where units from tetraalkoxysilanes are 0-100 weight percent of the network, where units from trialkoxysilanes are 0 to 100 weight percent of the network, and optionally comprising units from dialkoxysilanes at 0 to 99 weight percent of the network, where the polyhydroxy molecule has differing patterns and degrees of condensation, where optionally, the silicon-oxygen-silicon groups and the silicon-oxygen-carbons groups of the structure are replaced with metal-oxygen-metal groups and metal-oxygen-carbon groups of another metal where the another metal is aluminum, titanium, zirconium, or germanium from at least one aluminate precursor, titanate precursor, zirconate precursor, or germinate precursor, and where, optionally, the polyhydroxy units from sucrose are replaced with the polyhydroxy units of an another organic molecule comprising a multiplicity of hydroxyl groups.

2. The superpolar sorbent network according to claim 1, wherein the metal oxide precursor is a tetraalkoxysilane, trialkoxysilane, or a combination of at least one of the tetraalkoxysilane and trialkoxysilane with a dialkoxysilane.

3. The superpolar sorbent network according to claim 1, wherein the another organic molecule is Sucrose-6-phosphate, Sucrose6F-phosphate, 2-Cyanoethylsucrose, Sucralose, 1-Ketose, UDP-alpha-D-glucose, Uridine Diphosphate Glucose, Sorbitol, or any mixture thereof.

4. The superpolar sorbent network according to claim 1, wherein the metal oxide precursor is tetramethoxysilane and the polyhydroxy molecule comprises sucrose.

5. The superpolar sorbent network according to claim 1, wherein the metal oxide precursor is methyltrimethoxysilane and the polyhydroxy molecule comprises sucrose.

6. The superpolar sorbent network according to claim 1, wherein the at least one metal oxide precursor includes an unsubstituted or substituted arytrialkoxysilane.

7. The superpolar sorbent network according to claim 1, wherein the at least one metal oxide precursor includes an unsubstituted or substituted alkyltrialkoxysilane.

8. A sampling device or analytical device comprising a superpolar sorbent network according to claim 1, wherein the sampling device is an extraction device or a chromatography device.

9. The sampling device or analytical device according to claim 8, wherein the extraction device is a fiber superpolar microextraction fiber, superpolar microextraction tube, superpolar microextraction membrane, superpolar microextraction stir bar, superpolar microextraction fabric, superpolar microextraction capsule, or superpolar microextraction vial.

10. The sampling device or analytical device according to claim 8, wherein the extraction device is a solid phase extractor selected from a matrix solid phase dispersant, a magnetic solid phase extractor, or a dynamic fabric phase sorptive extractor.

11. The sampling device or analytical device according to claim 8, wherein the analytical device is a gas chromatograph or a liquid chromatograph.

12. A method of preparing a superpolar sorbent network according to claim 1, comprising:
   providing at least one metal oxide precursor;
   providing at least one polyhydroxy molecule;
   providing water;
   providing a catalyst;
   optionally, providing a solvent;
   combining the at least one metal oxide precursor, the at least one polyhydroxy molecule, the water, the catalyst, and, optionally, the solvent to form a sol;
   hydrolyzing the sol, wherein the at least one metal oxide precursors form hydrolyzed metal oxide precursors; and
   condensing the hydrolyzed metal oxide precursors and the at least one polyhydroxy molecules to form a gel that provides the superpolar sorbent network.

13. The method according to claim 12, wherein condensing occurs with heating of the sol.

14. The method according to claim 12, further comprising coating the sol on a substrate, wherein the superpolar sorbent network comprises a coating on the substrate.

15. The method according to claim 14, wherein the substrate is a metal oxide particle, a metal tube, a silica fiber, a fabric, a glass tube, a glass sheet, or a vial.

\* \* \* \* \*

UNITED STATES PATENT AND TRADEMARK OFFICE
CERTIFICATE OF CORRECTION

PATENT NO.         : 9,700,872 B1
APPLICATION NO.    : 15/200224
DATED              : July 11, 2017
INVENTOR(S)        : Abuzar Kabir and Kenneth G. Furton It is certified that error appears in the above-identified patent and that said Letters Patent is hereby corrected as shown below:

In the Specification

Column 4,
Lines 36-37, "3-aminoporpyltrimethoxysilane" should read --3-aminopropyltrimethoxysilane--.
Line 54, "dialkyldialkoxyslanes can" should read --dialkyldialkoxysilanes can--.
Line 62, "in the presences of" should read --in the presence of--.

Column 5,
Line 31, "tetralkoxysilane" should read --tetraalkoxysilane--.

Column 6,
Line 54, "2-Chroethyl vinyl ether" should read --2-Chloroethyl vinyl ether--.
Line 60, "C6H4Cl2" should read --$C_6H_4Cl_2$--.

Column 7,
Line 15, "CH3Cl" should read --$CH_3Cl$--.
Line 21, "C10H8" should read --$C_{10}H_8$--.

In the Claims

Column 10,
Line 37, in Claim 3 "Sucrose6F-phosphate" should read --Sucrose-6F-phosphate--.

Signed and Sealed this
Seventeenth Day of April, 2018

Andrei Iancu
*Director of the United States Patent and Trademark Office*